(12) United States Patent
Kogami et al.

(10) Patent No.: US 8,981,122 B2
(45) Date of Patent: Mar. 17, 2015

(54) METHOD FOR PRODUCING OPTICALLY ACTIVE N-MONOALKYL-3-HYDROXY-3-ARYLPROPYLAMINE COMPOUND

(75) Inventors: Kenji Kogami, Hyogo (JP); Shuzo Satake, Osaka (JP)

(73) Assignee: Sumitomo Seika Chemicals Co., Ltd., Kako-gun (JP)

( * ) Notice: Subject to any disclaimer, the term of this patent is extended or adjusted under 35 U.S.C. 154(b) by 0 days.

(21) Appl. No.: 13/583,376

(22) PCT Filed: Mar. 23, 2011

(86) PCT No.: PCT/JP2011/056971
§ 371 (c)(1),
(2), (4) Date: Sep. 7, 2012

(87) PCT Pub. No.: WO2011/118625
PCT Pub. Date: Sep. 29, 2011

(65) Prior Publication Data
US 2013/0005992 A1  Jan. 3, 2013

(30) Foreign Application Priority Data
Mar. 24, 2010  (JP) .................................. 2010-067904

(51) Int. Cl.
| | | |
|---|---|---|
| C07D 333/16 | (2006.01) | |
| C07B 53/00 | (2006.01) | |
| C07D 333/20 | (2006.01) | |
| C07D 333/22 | (2006.01) | |

(52) U.S. Cl.
CPC .............. *C07B 53/00* (2013.01); *C07D 333/16* (2013.01); *C07D 333/20* (2013.01); *C07D 333/22* (2013.01)
USPC .......................................................... 549/75

(58) Field of Classification Search
CPC .................................................... C07D 333/16
USPC ..................................................... 549/72, 75
See application file for complete search history.

(56) References Cited

U.S. PATENT DOCUMENTS

| | | | |
|---|---|---|---|
| 5,225,585 A | 7/1993 | Schwartz | |
| 2004/0082794 A1 | 4/2004 | Yokozawa | |
| 2005/0261514 A1 | 11/2005 | Kralik | |
| 2006/0167278 A1 | 7/2006 | Inoue | |

FOREIGN PATENT DOCUMENTS

| | | |
|---|---|---|
| EP | 0 457 559 A2 | 11/1991 |
| JP | H4-226948 | 8/1992 |
| JP | H5-213838 | 8/1993 |
| JP | 2004-123596 A1 | 4/2004 |
| JP | 2004-155770 A1 | 6/2004 |
| JP | 2005-536556 A1 | 12/2005 |
| WO | WO 03/097632 A1 | 11/2003 |
| WO | WO 2004/103990 A1 | 12/2004 |

OTHER PUBLICATIONS

S. Sakuraba, et al.; "Practical Asymmetric Synthesis of (R)-Fluoxetine Hydrochloride Catalyzed by (2S,4S)-4-Dicyclohexylphosphino-2-diphenylphosphinomethyl-1-(N-methycarbamoyl)pyrrolidine-Rhodium Complex;" Synlett; No. 10; Sep. 1991; pp. 689-690 and end sheet (3 Sheets)/Cited in International Search Report.
International Search Report for International Application No. PCT/JP2011/056971 dated Jun. 21, 2011.
English translation of the Japanese publication No. 2004-155770, published Jun. 3, 2004.

*Primary Examiner* — Taofiq A Solola
(74) *Attorney, Agent, or Firm* — Kratz, Quintos & Hanson, LLP

(57) ABSTRACT

The present invention provides a method for producing an N-monoalkyl-3-hydroxy-3-arylpropylamine compound represented by Formula (2):

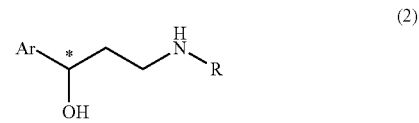

(2)

wherein Ar represents an optionally substituted aryl or an optionally substituted heteroaryl, R represents an optionally substituted $C_{1-5}$ alkyl, and * represents an asymmetric carbon atom; the method comprising: reacting, in the presence of an asymmetric reduction catalyst, hydrogen gas with an N-benzyl-N-monoalkyl-3-oxo-3-arylpropenylamine compound represented by Formula (1):

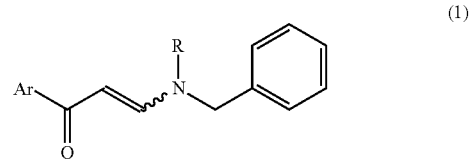

(1)

wherein Ar and R are as defined above. The present invention allows an optically active N-monoalkyl-3-hydroxy-3-arylpropylamine compound to be produced easily and inexpensively under industrially advantageous conditions.

6 Claims, No Drawings

METHOD FOR PRODUCING OPTICALLY ACTIVE N-MONOALKYL-3-HYDROXY-3-ARYLPROPYLAMINE COMPOUND

TECHNICAL FIELD

The present invention relates to a method for producing an optically active N-monoalkyl-3-hydroxy-3-arylpropylamine compound.

BACKGROUND ART

An N-monoalkyl-3-hydroxy-3-arylpropylamine compound is useful as an intermediate and the like for various medicines, etc. As one example of a method for producing an optically active compound thereof, racemic isomers thereof are subjected to optical resolution using a resolving agent, such as an optically active organic acid (Patent Literature 1). However, because this method uses optical resolution, only about half of the racemic isomers thereof can be used, making it disadvantageous in regard to yield. In addition, this method poses various problems, including the need to recycle a resolving agent.

In another known method, an N,N-dialkyl-3-hydroxy-3-arylpropylamine compound is dealkylated using a dealkylation agent (Patent Literature 2). However, this method is economically disadvantageous because it requires at least twice as much of the dealkylation agent in a molar ratio relative to the reactant.

CITATION LIST

Patent Literature

PTL 1: Japanese Unexamined Patent Publication No. 2004-123596
PTL 2: Japanese Unexamined Patent Publication No. H.5-213838

SUMMARY OF INVENTION

Technical Problem

The present invention was made in view of the problems of prior art techniques described above. A main object of the present invention is to provide a method for producing an optically active N-monoalkyl-3-hydroxy-3-arylpropylamine compound easily and inexpensively under industrially advantageous conditions.

Solution to Problem

In order to achieve the above object, the present inventors have conducted extensive research. As a result, they found that the target optically active N-monoalkyl-3-hydroxy-3-arylpropylamine compound can be produced inexpensively at a high yield through an industrially advantageous process by using an N-benzyl-N-monoalkyl-3-oxo-3-arylpropenylamine compound as a starting material and reacting it with hydrogen in the presence of an asymmetric reduction catalyst, allowing an asymmetric reduction and debenzylation reaction to progress.

More specifically, the present invention provides the following methods for producing an optically active N-monoalkyl-3-hydroxy-3-arylpropylamine compound.

1. A method for producing an N-monoalkyl-3-hydroxy-3-arylpropylamine compound represented by Formula (2):

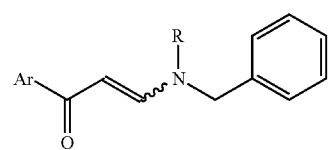

wherein Ar represents an optionally substituted aryl or an optionally substituted heteroaryl, R represents an optionally substituted $C_{1-5}$ alkyl, and * represents an asymmetric carbon atom;

the method comprising reacting hydrogen gas with an N-benzyl-N-monoalkyl-3-oxo-3-arylpropenylamine compound represented by Formula (1):

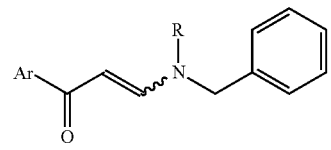

wherein Ar and R are the same as defined above, in the presence of an asymmetric reduction catalyst.

2. The method according to Item 1, wherein the asymmetric reduction catalyst is a transition metal complex.

3. The method according to Item 1 or 2, wherein the reaction is conducted also in the presence of a base.

The process for producing the optically active N-monoalkyl-3-hydroxy-3-arylpropylamine compound of the present invention is explained in detail below.

Raw Material Compound

In the production method of the present invention, the N-benzyl-N-monoalkyl-3-oxo-3-arylpropenylamine compound represented by Formula (1) below is used as a raw material:

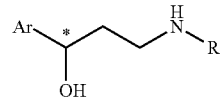

wherein Ar represents an optionally substituted aryl or an optionally substituted heteroaryl, and R represents an optionally substituted $C_{1-5}$ alkyl. In Formula (1), the substitution site on the carbon-carbon double bond may be either cis position or trans position.

The compound is known and can be obtained by reacting, for example, an aqueous solution of N-alkyl-N-benzylamine hydrochloride and an alkaline metal salt of β-oxo-β-(aryl or heteroaryl)propanal.

In Formula (1), examples of aryl groups represented by Ar include phenyl, naphthyl, phenanthryl, and the like. Examples of heteroaryl groups include furyl, thienyl, pyrrolyl, pyridyl, benzofuryl, indenyl, and the like.

Examples of $C_{1-5}$ alkyl groups represented by R include methyl, ethyl, n-propyl, isopropyl, n-butyl, isobutyl, tert-butyl, n-pentyl, and like linear or branched $C_{1-5}$ alkyl groups.

The aryl groups, heteroaryl groups and alkyl groups mentioned above may include one or more substituents. When they include two or more substituents, the substituents may be the same or different. Examples of such substituents include hydroxy, methyl, ethyl, propyl, trifluoromethyl, methoxy, nitro, amino, methylsulfonylamino, benzoyloxy, fluorine atom, chlorine atom, bromine atom, iodine atom, and the like.

Specific examples of N-benzyl-N-monoalkyl-3-oxo-3-arylpropenylamine compounds represented by Formula (1) include N-methyl-N-benzyl-3-oxo-3-phenylpropenylamine, N-ethyl-N-benzyl-3-oxo-3-(4-toluyl)propenylamine, N-ethyl-N-benzyl-3-oxo-3-(4-trifluoromethylphenyl)propenylamine, N-methyl-N-benzyl-3-oxo-3-(4-methoxyphenyl) propenylamine, N-(n-propyl)-N-benzyl-3-oxo-3-(4-nitrophenyl)propenylamine, N-(tert-butyl)-N-benzyl-3-oxo-3-(3-methylsulfonylaminophenyl)propenylamine, N-methyl-N-benzyl-3-oxo-3-(4-benzoyloxyphenyl)propenylamine, N-ethyl-N-benzyl-3-oxo-3-(4-chlorophenyl)propenylamine, N-methyl-N-benzyl-3-oxo-3-(4,6-dimethoxy-9-phenanthryl)propenylamine, (n-pentyl)-N-benzyl-3-oxo-3-[1,3-dichloro-6-(trifluoromethyl)-9-phenanthryl]propenylamine, N-methyl-N-benzyl-3-oxo-3-(2-chloro-5-thienyl)propylamine, N-ethyl-N-benzyl-3-oxo-3-(2-thienyl)propenylamine, N-methyl-N-benzyl-3-oxo-3-(2-thienyl)propenylamine, N-methyl-N-benzyl-3-oxo-3-(2-thienyl) propenylamine, N-methyl-N-benzyl-3-oxo-3-(3-thienyl) propenylamine, N-methyl-N-benzyl-3-oxo-3-(4-methyl-2-thienyl)propenylamine, N-methyl-N-benzyl-3-oxo-3-(2-chloro-6-pyridyl)propenylamine, N-methyl-N-benzyl-3-oxo-3-(2-pyridyl)propenylamine, N-ethyl-N-benzyl-3-oxo-3-(2-benzofuryl)propenylamine, and the like.

Method for Producing N-Monoalkyl-3-Hydroxy-3-Arylpropylamine Compound

The optically active N-monoalkyl-3-hydroxy-3-arylpropylamine compound targeted by the present invention is represented by Formula (2) shown below:

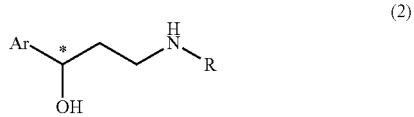

(2)

wherein Ar represents an optionally substituted aryl or an optionally substituted heteroaryl, R represents an optionally substituted $C_{1-5}$ alkyl, and * represents an asymmetric carbon atom.

The N-monoalkyl-3-hydroxy-3-arylpropylamine compound can be obtained by reacting an N-benzyl-N-monoalkyl-3-oxo-3-arylpropenylamine compound represented by Formula (1) described above with hydrogen in the presence of an asymmetric reduction catalyst.

In this method, an asymmetric reduction and debenzylation reaction proceed by a simple method wherein a raw material compound is reacted with hydrogen gas. This allows an optically active N-monoalkyl-3-hydroxy-3-arylpropylamine compound represented by Formula (2) to be produced with high purity in an inexpensive manner. Therefore, the method of the present invention is industrially very advantageous for producing an optically active N-monoalkyl-3-hydroxy-3-arylpropylamine compound.

In the present invention, the asymmetric reduction catalyst is not particularly limited and various transition metal complexes can be used. Examples of usable asymmetric reduction catalysts include $RuCl_2[(S)-BINAP][(S,S)-DPEN]$, $RuCl_2[(S)-BINAP][(R,R)-DAIPEN]$, $RuCl_2[(S)-BINAP][(R,R)-DPEN]$, $RuCl_2[(R)-BINAP][(S,S)-DPEN]$, $RuCl_2[(R)-BINAP][(R,R)-DPEN]$, $RuCl_2[(R)-BINAP][(R)-DAIPEN]$, $RuCl_2[(S)-Tol-BINAP][(S,S)-DPEN]$, $RuCl_2[(S)-Tol-BINAP][(S)-DAIPEN]$, $RuCl_2[(S)-Tol-BINAP][(R,R)-DPEN]$, $RuCl_2[(R)-Tol-BINAP][(S,S)-DPEN]$, $RuCl_2[(R)-Tol-BINAP][(R,R)-DPEN]$, $RuCl_2[(R)-Tol-BINAP][(R)-DAIPEN]$, and the like.

Here, BINAP stands for 2,2'-bis-(diphenylphosphino)-1,1'-binaphthyl; Tol-BINAP stands for 2,2'-bis-(di-tolylphenylphosphino)-1,1'-binaphthyl; DPEN stands for 1,2-diphenylethylenediamine; and DAIPEN stands for 1,1-di(4-anisyl)-2-isopropyl-1,2-ethylenediamine.

The amount of the asymmetric reduction catalyst used is preferably about 0.0001 to 0.1 mol and more preferably about 0.0005 to 0.02 mol per mole of the N-benzyl-N-monoalkyl-3-oxo-3-arylpropenylamine compound represented by Formula (1).

The reaction between the N-benzyl-N-monoalkyl-3-oxo-3-arylpropenylamine compound represented by Formula (1) and hydrogen can be conducted by blowing hydrogen gas into a solution or dispersion comprising an N-benzyl-N-monoalkyl-3-oxo-3-arylpropenylamine compound and an asymmetric carbon catalyst dissolved or dispersed therein, or by charging hydrogen gas into a reaction vessel in which the solution or dispersion is contained.

The pressure of the hydrogen gas is preferably about 0.001 to 150 MPa, and more preferably about 0.1 to 100 MPa.

Examples of reaction solvents include methanol, ethanol, 2-propanol, and like alcohols; methylene chloride, 1,2-dichloroethane, and like halogenated hydrocarbons; diethyl ether, tert-butyl methyl ether, and like ethers.

The amount of reaction solvent is preferably about 1 to 1,000 parts by weight and more preferably about 5 to 100 parts by weight per part by weight of the N-benzyl-N-monoalkyl-3-oxo-3-arylpropenylamine compound represented by Formula (1).

The reaction temperature is preferably about −20 to 150° C. and more preferably about 0 to 100° C.

The reaction time is generally about 1 to 24 hours.

A base may be added to the reaction solvent if necessary. Examples of bases include lithium hydroxide, sodium hydroxide, potassium hydroxide, calcium hydroxide, and like metal hydroxides; sodium methoxide, potassium ethoxide, tert-butoxysodium, tert-butoxypotassium, and like metal alkoxides; potassium hydride, sodium hydride, and like metal hydrides; etc. By adding a base, the reaction time can be shortened and the reaction can easily progress, resulting in further lowering the hydrogen gas pressure.

The proportion of the base used is preferably about 0.1 to 10 mol and more preferably about 0.5 to 4 mol per mole of the asymmetric reduction catalyst.

By reacting the N-benzyl-N-monoalkyl-3-oxo-3-arylpropenylamine compound represented by Formula (1) with hydrogen according to the method described above, a reaction solution containing the optically active N-monoalkyl-3-hydroxy-3-arylpropylamine compound represented by Formula (2) can be obtained.

The target N-monoalkyl-3-hydroxy-3-arylpropylamine compound can be isolated from the reaction solution by, for example, condensing, adding water, and toluene, diethyl ether, or a like water-insoluble solvent to the resulting residue, further adding alkali to make the aqueous layer basic, followed by liquid-liquid separation to obtain the organic layer, and condensing the resulting organic layer. Furthermore, the resulting N-monoalkyl-3-hydroxy-3-arylpropylamine compound can be purified by silica gel column chromatography, distillation, or a like method.

Thus, the optically active N-monoalkyl-3-hydroxy-3-arylpropylamine compound represented by Formula (2) can be obtained:

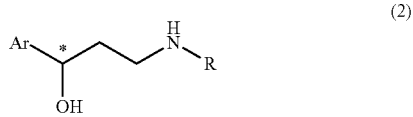

wherein Ar and R are the same as defined above, and * represents an asymmetric carbon atom.

Specific examples of the N-monoalkyl-3-hydroxy-3-arylpropylamine compounds include N-methyl-3-hydroxy-3-phenylpropylamine, N-ethyl-3-hydroxy-3-(4-toluyl)propylamine, N-ethyl-3-hydroxy-3-(4-trifluoromethylphenyl)propylamine, N-methyl-3-hydroxy-3-(4-methoxypheny)propylamine, N-(n-propyl)-3-hydroxy-3-(4-nitrophenyl)propylamine, N-(tert-butyl)-3-hydroxy-3-(3-methylsulfonylaminophenyl)propylamine, N-methyl-3-hydroxy-3-(4-benzoyloxyphenyl)propylamine, N-ethyl-3-hydroxy-3-(4-chlorophenyl)propylamine, N-methyl-3-hydroxy-3-(4,6-dimethoxy-9-phenanthryl)propylamine, N-(n-pentyl)-3-hydroxy-3-[1,3-dichloro-6-(trifluoromethyl)-9-phenanthryl]propylamine, N-methyl-3-hydroxy-3-(2-chloro-5-thienyl)propylamine, N-ethyl-3-hydroxy-3-(2-thienyl)propylamine, N-methyl-3-hydroxy-3-(2-thienyl)propylamine, N-methyl-3-hydroxy-3-(3-thienyl)propylamine, N-methyl-3-hydroxy-3-(4-methyl-2-thienyl)propylamine, N-methyl-3-hydroxy-3-(2-chloro-6-pyridyl)propylamine, N-methyl-3-hydroxy-3-(2-pyridyl)propylamine, N-ethyl-3-hydroxy-3-(2-benzofuryl)propylamine, and the like.

Advantageous Effects of Invention

The production method of the present invention makes it possible to produce an optically active N-monoalkyl-3-hydroxy-3-arylpropylamine compound usable as, for example, an intermediate for various medicines, etc., by a simple production process with high purity and in an inexpensive manner. Therefore, the method of the present invention is industrially advantageous as a method for producing an optically active N-monoalkyl-3-hydroxy-3-arylpropylamine compound.

DESCRIPTION OF EMBODIMENTS

The present invention is explained in detail below with reference to Production Examples and Examples. However, the scope of the present invention is not limited to these Production Examples and Examples.

Production Example 1

Sodium salt of β-oxo-β-(2-thienyl)propanal (88.1 g, 0.50 mol) and methanol (168 g) were placed in a 1-liter, four-necked flask equipped with a stirrer, a condenser, a thermometer and a dropping funnel, and an aqueous solution of N-methyl-N-benzylamine hydrochloride (0.50 mol) was added dropwise thereto at 10° C. over a period of 30 minutes. After the dropwise addition was completed, the mixture was allowed to react at 30° C. for 5 hours.

After the reaction was completed, methanol was distilled off. Thereafter, 121.4 g of a 3.1% by weight aqueous solution of sodium hydroxide and 100 g of methyl tert-butyl ether were added thereto, and the resulting mixture was subjected to liquid-liquid separation to obtain the organic layer. The solvent was distilled off from the organic layer, and the deposited crystals were separated by filtration. By washing the resulting crystals with 100 g of ethanol twice and drying it, 105.5 g (0.420 mol) of N-methyl-N-benzyl-3-oxo-3-(2-thienyl)propenamine was obtained. The yield of the N-methyl-N-benzyl-3-oxo-3-(2-thienyl)propenamine relative to sodium salt of β-oxo-β-(2-thienyl)propanal was 84%.

Production Example 2

111.3 g (0.410 mol) of N-ethyl-N-benzyl-3-oxo-3-(2-thienyl)propenamine was produced in the same manner as in Production Example 1 except that an aqueous solution of N-ethyl-N-benzylamine hydrochloride (0.50 mol) was used instead of the aqueous solution of N-methyl-N-benzylamine hydrochloride (0.50 mol). The yield of the N-ethyl-N-benzyl-3-oxo-3-(2-thienyl)propenamine relative to sodium salt of β-oxo-β-(2-thienyl)propanal was 82%.

Example 1

Under an argon atmosphere, the N-methyl-N-benzyl-3-oxo-3-(2-thienyl)propenylamine (128.7 mg, 0.50 mmol) obtained in Production Example 1, an RuCl$_2$[(R)-BINAP][(R)-DAIPEN] complex (5.5 mg, 0.0050 mmol) and 2-propanol (2 ml) were placed in a 20-ml two-necked flask, and 20 μl of a 2-propanol solution of tert-butoxypotassium (concentration: 0.5 mol/L) was added thereto. Subsequently, hydrogen was charged therein at a pressure of 1 MPa, and the resulting mixture was allowed to react at 80° C. for 16 hours.

After the reaction was completed, the reaction mixture was concentrated and the residue was purified by silica gel column chromatography to obtain 68.5 mg (0.40 mmol) of (S)—N-methyl-3-hydroxy-3-(2-thienyl)propylamine. The yield of the obtained (S)—N-methyl-3-hydroxy-3-(2-thienyl)propylamine relative to N-methyl-N-benzyl-3-oxo-3-(2-thienyl)propenylamine was 80%.

The optical purity of the obtained (S)—N-methyl-3-hydroxy-3-(2-thienyl)propylamine determined using high-performance-liquid-chromatography was 99% ee.

Example 2

76.0 mg (0.41 mmol) of (S)—N-ethyl-3-hydroxy-3-(2-thienyl)propylamine was produced in the same manner as in Example 1 except that N-ethyl-N-benzyl-3-oxo-3-(2-thienyl)propenylamine (135.7 mg, 0.50 mmol) obtained in Production Example 2 was used instead of N-methyl-N-benzyl-3-oxo-3-(2-thienyl)propenylamine (128.7 mg, 0.50 mmol). The yield of the obtained (S)—N-ethyl-3-hydroxy-3-(2-thienyl)propylamine relative to the N-ethyl-N-benzyl-3-oxo-3-(2-thienyl)propenylamine was 82%.

The optical purity of the obtained (S)—N-ethyl-3-hydroxy-3-(2-thienyl)propylamine determined using high-performance-liquid-chromatography was 99% ee.

The invention claimed is:
1. A method for producing an N-monoalkyl-3-hydroxy-3-arylpropylamine compound represented by Formula (2):

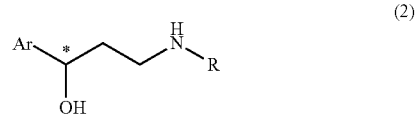

wherein Ar represents an optionally substituted aryl or an optionally substituted heteroaryl, R represents an optionally substituted $C_{1-5}$ alkyl, and * represents an asymmetric carbon atom;

the method comprising reacting hydrogen gas with an N-benzyl-N-monoalkyl-3-oxo-3-arylpropenylamine compound represented by Formula (1):

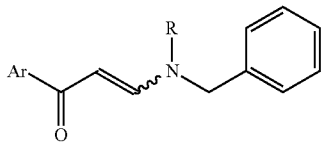

(1)

wherein Ar and R are the same as defined above, in the presence of at least one asymmetric reduction catalyst selected from the group consisting of
$RuCl_2$[(S)-BINAP][(S,S)-DPEN], $RuCl_2$[(S)-BINAP][(S)-DAIPEN], $RuCl_2$[(S)-BINAP][(R,R)-DPEN], $RuCl_2$[(R)-BINAP][(S,S)-DPEN], $RuCl_2$[(R)-BINAP][(R,R)-DPEN], $RuCl_2$[(R)-BINAP][(R)-DAIPEN], $RuCl_2$[(S)-Tol-BINAP][(S,S)-DPEN], $RuCl_2$[(S)-Tol-BINAP][(S)-DAIPEN], $RuCl_2$[(S)-Tol-BINAP][(R,R)-DPEN], $RuCl_2$[(R)-Tol-BINAP][(S,S)-DPEN], $RuCl_2$[(R)-Tol-BINAP][(R,R)-DPEN], and $RuCl_2$[(R)-Tol-BINAP][(R)-DAIPEN].

2. The method according to claim 1, wherein the amount of the asymmetric reduction catalyst is 0.0001 to 0.1 mol per mole of the N-benzyl-N-monoalkyl-3-oxo-3-arylpropenylamine compound represented by Formula (1).

3. The method according to claim 1, wherein the reaction is performed in solvent selected from the group consisting of alcohol, halogenated hydrocarbon, and ether.

4. The method according to claim 1, wherein the reaction is performed in alcohol.

5. The method according to claim 1, wherein the reaction is performed in the presence of at least one base selected from the group consisting of a metal hydroxide and a metal alkoxide.

6. The method according to claim 1, wherein the reaction is performed in the presence of a metal alkoxide.

* * * * *